US007851207B1

(12) United States Patent
Sagripanti

(10) Patent No.: US 7,851,207 B1
(45) Date of Patent: Dec. 14, 2010

(54) MULTIPLEX FIELD DEVICE TO DETECT AND IDENTIFY A VARIETY OF MICROBIAL AGENTS SIMULTANEOUSLY

(75) Inventor: Jose-Luis Sagripanti, Belair, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 487 days.

(21) Appl. No.: 11/852,489

(22) Filed: Sep. 10, 2007

Related U.S. Application Data

(60) Provisional application No. 60/888,669, filed on Feb. 7, 2007.

(51) Int. Cl.
*C12M 1/34* (2006.01)
*C12M 3/00* (2006.01)

(52) U.S. Cl. .................. 435/288.2; 435/7.92; 435/91.2; 435/287.2; 435/303.1; 422/58; 422/72

(58) Field of Classification Search ................ 435/7.92, 435/91.2, 287.2, 303.1, 288.2; 422/58, 72; 137/814, 820, 829
See application file for complete search history.

(56) References Cited

U.S. PATENT DOCUMENTS

| | | | | |
|---|---|---|---|---|
| 5,607,860 | A * | 3/1997 | Gombrich et al. | 435/287.3 |
| 7,405,073 | B2 * | 7/2008 | Tilles et al. | 435/287.1 |
| 2008/0131949 | A1 * | 6/2008 | Bortolin et al. | 435/173.9 |

* cited by examiner

*Primary Examiner*—William H Beisner
*Assistant Examiner*—Michael Hobbs
(74) *Attorney, Agent, or Firm*—Ulysses John Biffoni

(57) ABSTRACT

The invention relates to methods and devices enabling simultaneous detection of several biological threat agents, including viruses and bacteria. The device includes a plurality of chambers and conduits which can be manually operated to so that reagents and sample are passed through the device and nucleic acid hybridization membranes to permit detection by the naked eye. The device has minimal logistical requirements since it is self-contained and includes all the reagents required to process a sample suspected of containing a variety of biological threat agents, it does not require electrical or other external sources of energy, it is disposable, and it can operated by a soldier or responder without microbiological training or expertise.

19 Claims, 5 Drawing Sheets

MULTIPLEX FIELD DEVICE TO DETECT AND IDENTIFY A VARIETY OF MICROBIAL AGENTS SIMULTANEOUSLY

RELATED APPLICATIONS

This application claims the benefit of priority from U.S. provisional application Ser. No. 60/888,669, filed on Feb. 7, 2007.

GOVERNMENT INTEREST

The invention described herein may be manufactured, used, and licensed by or for the United States Government.

FIELD OF THE INVENTION

This invention relates to devices, kits and methods enabling simultaneous detection of several biological threat agents, including viruses and bacteria, during combat or in suspected contaminated samples or locations. The present invention allows such detection by selectively binding the nucleic acids of such biological threat agents to a solid substrate and allows an operator to inspect the solid substrate for color patterns, preferably by eye.

BACKGROUND OF THE INVENTION

With increasing terrorist activities occurring around the world, new technologies must be developed enabling the detection of biological threat agents both in combat and civilian environments. Current detection methods identifying biological threat agents, such as viruses and bacteria, use ELISA (enzyme linked immunological assay) and PCR (polymerase chain reaction, based on nucleic acid amplification) as operative core platforms. Such detection methods work well in hospitals or other medical institutions but are not as well suited for biodefense applications. ELISA and other antibody-based methods require stable antibodies and enzymes, which have low stability after deployment and therefore do not last long during combat or during long transports to suspected compromised areas. PCR methods require thermal cyclers, energy supply sources, and a large logistic footprint that either consumes resources needed in other tasks or requires sensitive equipment that is not easy to transport.

In addition, ELIZA and PCR based detection methods are limited in that they are not able to detect multiple threat agents at once, particularly under conditions encountered in combat or a threat situation. One is able to detect several virus types using PCR, but the amount of virus types that can be detected at once is limited by the number of fluorochromes that are available for differentiating. In addition, PCR multiplexing techniques are generally expensive and require delicate equipment that is not easily transported. PCR multiplexing is costly, complex, and does not function well to analyze the massive amounts of agent present after a biological attack.

SUMMARY OF THE INVENTION

Accordingly, it is an object of the present invention to meet the foregoing needs by providing detection devices, kits, and methods capable of detecting one or more biological threat agents simultaneously in a simple and cost effective manner. A suspect sample (a sample thought to contain a biological threat agent) may be obtained from a combat location or a civilian threat location. The methods and devices of the present invention preferably enable the identification of one or more biological threat agents by simple visual inspection of a detection means. The devices, kits, and methods of the present invention can be easily performed without extensive training of an operator, complex equipment, or vast logistic support. The operator of the methods and devices of the present invention include soldiers having little or no training in microbiology or virology.

One embodiment of the present invention is a multiplex field device for detecting biological threat agents comprising: (a) a central capped chamber having a top, a bottom, a connecting conduit PC, a connecting conduit WC, wherein the connecting conduit PC and the connecting conduit WC are located between the top and the bottom; (b) a plurality of peripheral chambers including, a first peripheral chamber including a first aperture; a second peripheral chamber including a second aperture; a third peripheral chamber including a third aperture; a fourth peripheral chamber including three apertures, aperture Q, aperture R, and aperture S, respectively; a fifth peripheral chamber including a fifth aperture; and a sixth peripheral chamber including a sixth aperture; (c) a first tube connecting the fourth peripheral chamber to the fifth peripheral chamber; (d) a second tube connecting the fourth peripheral chamber to the sixth peripheral chamber; and (e) a waste chamber including three apertures, aperture A, aperture B, and aperture C, respectively. The multiplex field device may further comprise a material moving means selected from the group comprising a vacuum, a syringe, or an embolus. The central capped chamber preferably contains a filter and a first solid support or membrane between its top and its bottom. It is preferable that the central chamber of the present invention be able to rotate on an axis. In addition, the multiplex field device is designed so that the connecting conduit PC is able to align with the first aperture, the second aperture, the third aperture, the fifth aperture, or the sixth aperture one at a time as the central chamber is rotated around the axis. In addition, the connecting conduit WC is able to align with aperture Q, aperture R, aperture S, aperture A, aperture B or aperture C one at a time as the central chamber is rotated around the axis. Also, it is preferable that a second solid support or membrane is located in the fourth peripheral chamber, wherein one or more capture nucleic acid sequences are attached to the second solid support.

Another embodiment of the present invention is a multiplex field device for detecting biological threat agents comprising: (a) a central capped chamber having a top, a bottom, a connecting conduit PC, a connecting conduit WC, a first solid support or membrane, and a filter; (b) a plurality of peripheral chambers including, a first peripheral chamber including a first aperture; a second peripheral chamber including a second aperture; a third peripheral chamber including a third aperture; a fourth peripheral chamber including three apertures comprising aperture Q, aperture R, and aperture S, respectively; a fifth peripheral chamber including a fifth aperture; and a sixth peripheral chamber including a sixth aperture; (c) a first tube connecting the fourth peripheral chamber to the fifth peripheral chamber; (d) a second tube connecting the fourth peripheral chamber to the sixth peripheral chamber; (e) said fourth peripheral chamber further comprising a second solid support or membrane; and (f) a waste chamber including three apertures, aperture A, aperture B, and aperture C, respectively, and wherein the central chamber is able to rotate on its axis. It is preferable that this device further comprise a material moving means selected from the group comprising a vacuum, a syringe, or an embolus. In addition, one or more capture nucleic acid sequences are attached to the second solid support or membrane and the central chamber of the device is able to rotate on an axis. In addition, the connecting conduit PC is able to align with the first aperture, the second aperture, the third aperture, the fifth aperture, or the sixth aperture one at a time as the central chamber is rotated on its axis, and the connecting conduit WC is able to align with aperture Q, aperture R, aperture S, aperture A, aperture B or aperture C one at a time as the central chamber is rotated on its axis. It is also preferable that the first solid support comprise a nucleic acid hybridization membrane.

Another embodiment of the present invention is a kit comprising the multiplex field device as described above; and materials comprising a diluting buffer present in the first peripheral chamber, a wash buffer present in the second peripheral chamber, an eluting buffer present in the third peripheral chamber; a hybridization buffer present in the fourth peripheral chamber; a hybridization wash buffer present in the fifth peripheral chamber, and a labeling buffer present in the sixth peripheral chamber. It is preferable that the kit includes a material moving means and that the labeling buffer further comprises digoxenin.

Another embodiment of the present invention is a method of detecting a biological threat agent comprising: (a) obtaining a suspect sample; (b) placing the suspect sample into the central chamber of said kit; (c) rotating the central capped chamber so that diluting buffer is moved into the interior of the central capped chambered and then moved into the waste chamber; (d) rotating the central capped chamber so that wash buffer is moved into the interior of the central capped chamber and then moved out into the waste chamber; (e) rotating the central capped chamber so that eluting buffer is moved into the interior space of the central capped chamber and then is moved out so as to come in contact with the second solid support in the fourth peripheral chamber; (f) rotating the central capped chamber so that the hybridization wash is moved into and contacts the second solid support and then is moved into the waste chamber; (g) rotating the central capped chamber so that the labeling buffer is moved into and contacts the second solid support; (h) visually inspecting the solid support; and (i) identifying the biological threat agent. The suspect sample may be obtained from a combat or civilian situation, where biological threat agents may be present.

BRIEF DESCRIPTION OF THE DRAWINGS

The accompanying drawings, which are incorporated in and constitute a part of this specification, illustrate embodiments of the present invention and, together with the description, explain the advantages and principles of the invention.

DETAILED DESCRIPTION OF THE INVENTION

Reference will now be made to preferred embodiments of this invention, examples of which will be clear from the detailed description of the invention. The present invention relates to methods and devices in which one or more biological threat agents may be identified in a combat or civilian threat situation. In order to better understand the invention the following terms have been defined:

"Biological Threat Agent" shall mean a biological entity that is a threat to life or health including viruses and bacteria, for example.

"Capture Nucleic Acid" is a nucleic acid, RNA or DNA, derived from a biological threat agent and attached to a solid support.

"Combat Situation" is any situation requiring biodefense such as military combat or a civilian terrorist attack wherein biological threat agents are implemented and require detection.

"Suspect Sample" is a sample thought to contain a biological threat agent.

"Target Nucleic Acid" is a nucleic acid, RNA or DNA, derived from a biological threat agent from a suspect sample.

The Multiplex Field Device

Central, Peripheral, and Waste Chambers

Figure 1:
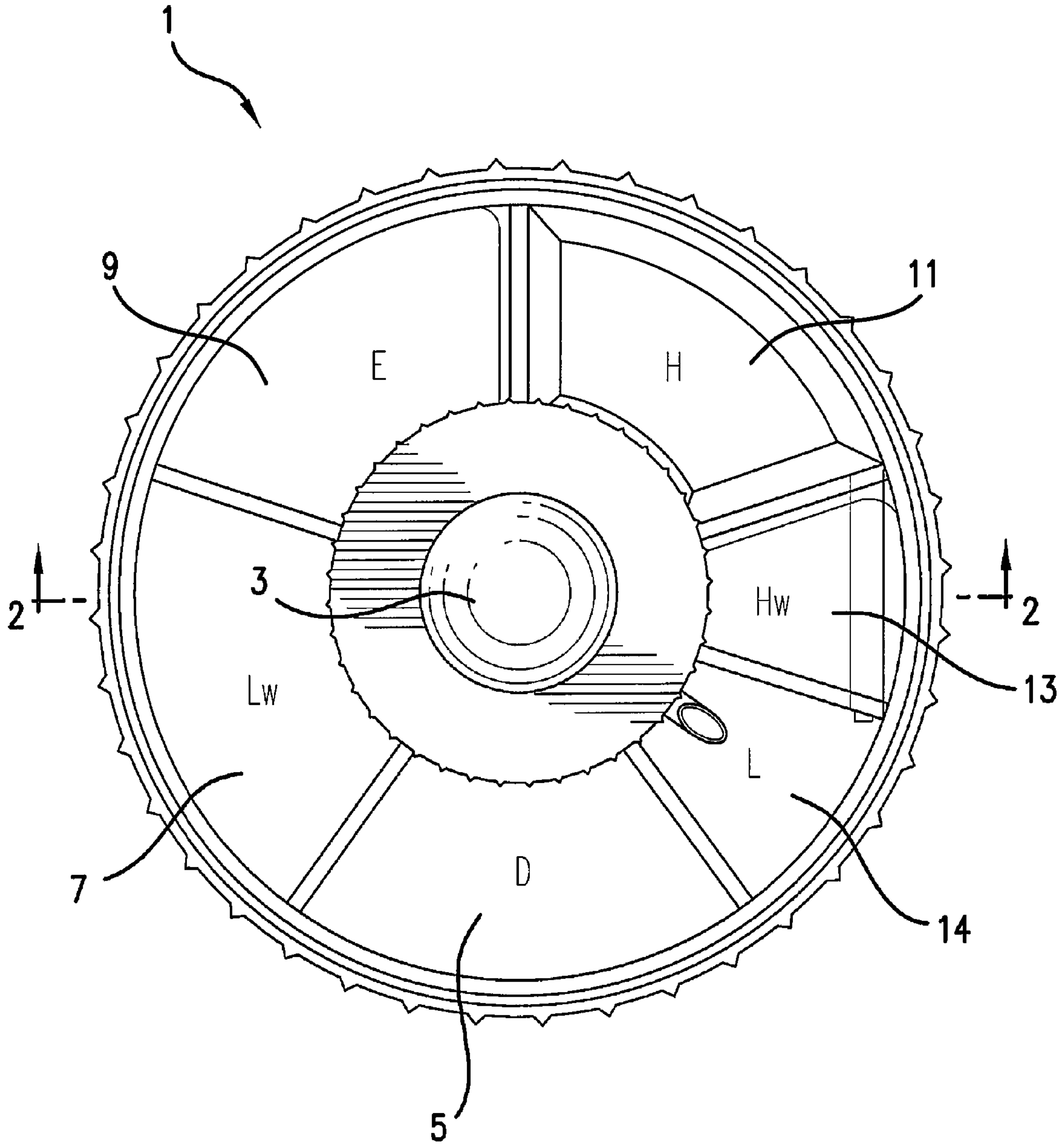
FIG. 1 is a top view of the Multiplex Field Device of the present invention.
Figure 2:
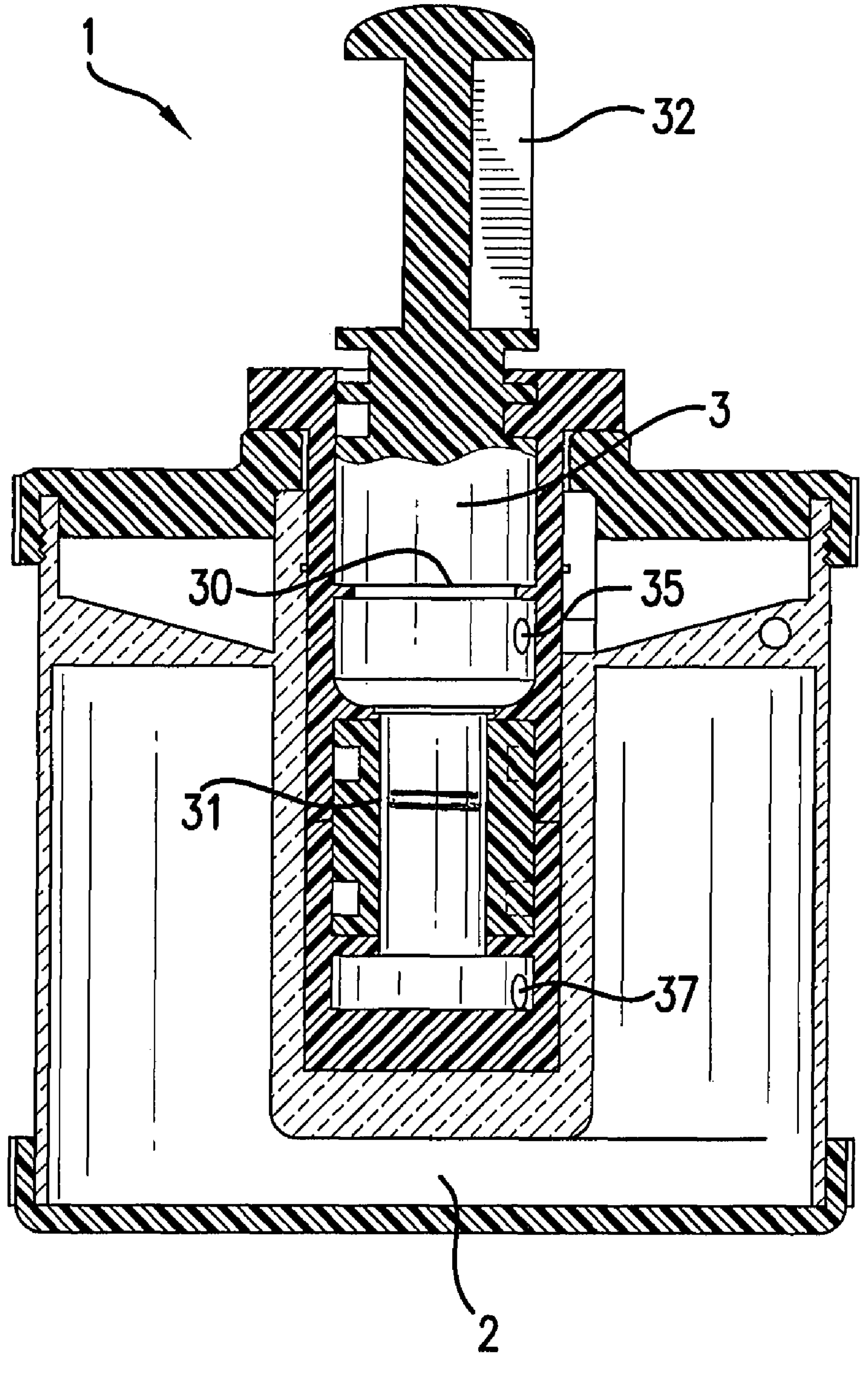
FIG. 2 is a sectional side view taken along 2-2 of FIG. 1 of the Multiplex Field Device of the present invention.

As shown in FIG. 1, the multiplex field device includes a multi-chambered system 1, which is preferably made of transparent plastic such as polypropylene, polycarbonate, Plexiglas, fluoroplastics, or polymethylpentene. This multi-chambered system preferably has a central capped chamber 3, preferably having a cylindrical shape, and several peripheral chambers: peripheral chamber (D) 5, peripheral chamber (Lw) 7, peripheral chamber (E) 9, peripheral chamber (H) 11, peripheral chamber (Hw), and peripheral chamber (L) 14. Another chamber, the waste chamber 2, is shown in FIG. 2. It is preferred that each peripheral chamber contains a material such as a liquid, solution, buffer, etc. prior to the use of the device of the present invention. More specifically, peripheral chamber (D) 5 is for containing diluting buffer, peripheral chamber (Lw) 7 is for containing wash buffer, peripheral chamber (E) 9 is for containing eluting material, peripheral chamber (H) 11 is for containing hybridization buffer, peripheral chamber (Hw) 13 is for containing hybridization wash buffer, and peripheral chamber (L) 14 is used for containing labeling buffer. The rotation of the central capped chamber 3 will allow material to move from one peripheral chamber to the waste chamber 2 or the peripheral hybridization chamber 11. The central chamber 3 is located central to the peripheral chambers 5, 7, 9, 11, 13, and 14, and the waste chamber 2, as shown in FIGS. 1 through 5. As shown in FIG. 2, located on the sides of the central capped chamber 3 and between the top and bottom are at least two connecting conduits: connecting conduit (PC) 35 and connecting conduit (WC) 37. As shown in FIG. 2, it is preferred that a filter 30 and a first solid support or membrane 31 are attached to the central capped chamber 3 between the top and bottom of the central capped chamber 3. Alternatively, the filter 30 and first solid support 31 could be packaged as part of a kit and attached to the central capped chamber 3 prior to use.

Figure 3:
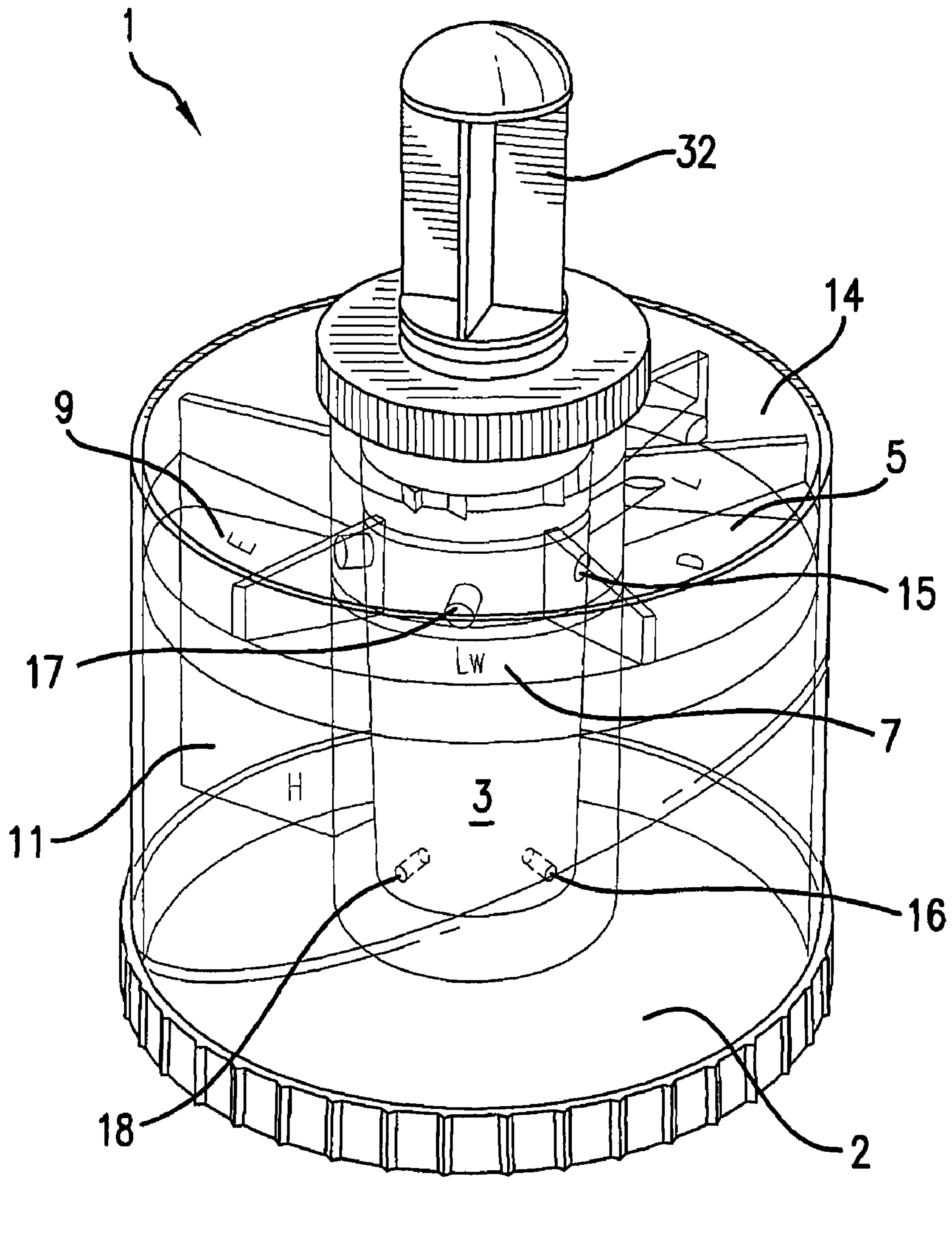
FIG. 3 is a first perspective view of the Multiplex Field Device of the present invention.

As shown in FIG. 3, it is preferable that the central chamber 3 contain moving means 32 such as a pump, syringe, or like means associated with the present invention for purposes of facilitating the movement of materials from the peripheral chambers, through the interior space of the central capped chamber 3, into the waste chamber 2, into the peripheral chamber (H) 11, or through tubes that are present in the present invention as described below.

In addition, the first solid support 31 and the filter 30 are preferably associated with the central capped chamber 3 between its bottom and top, with filter 30 preferably located above the connecting conduit (PC) 35 and also located between the binding membrane 31 and moving means 32. This filter 30 acts as a sieve preventing coarse environmental contaminants from clogging the first solid support 31. The first solid support 31 or membrane is located closer to the bottom of the central capped chamber 3 than the filter 30. The first solid support 31 can be employed horizontally as described or vertically (allowing liquid contact by capillarity) without departing from the spirit of this invention. A second solid support or membrane 29 is located in the peripheral hybridization chamber 11.

Peripheral Chambers

Figure 4:
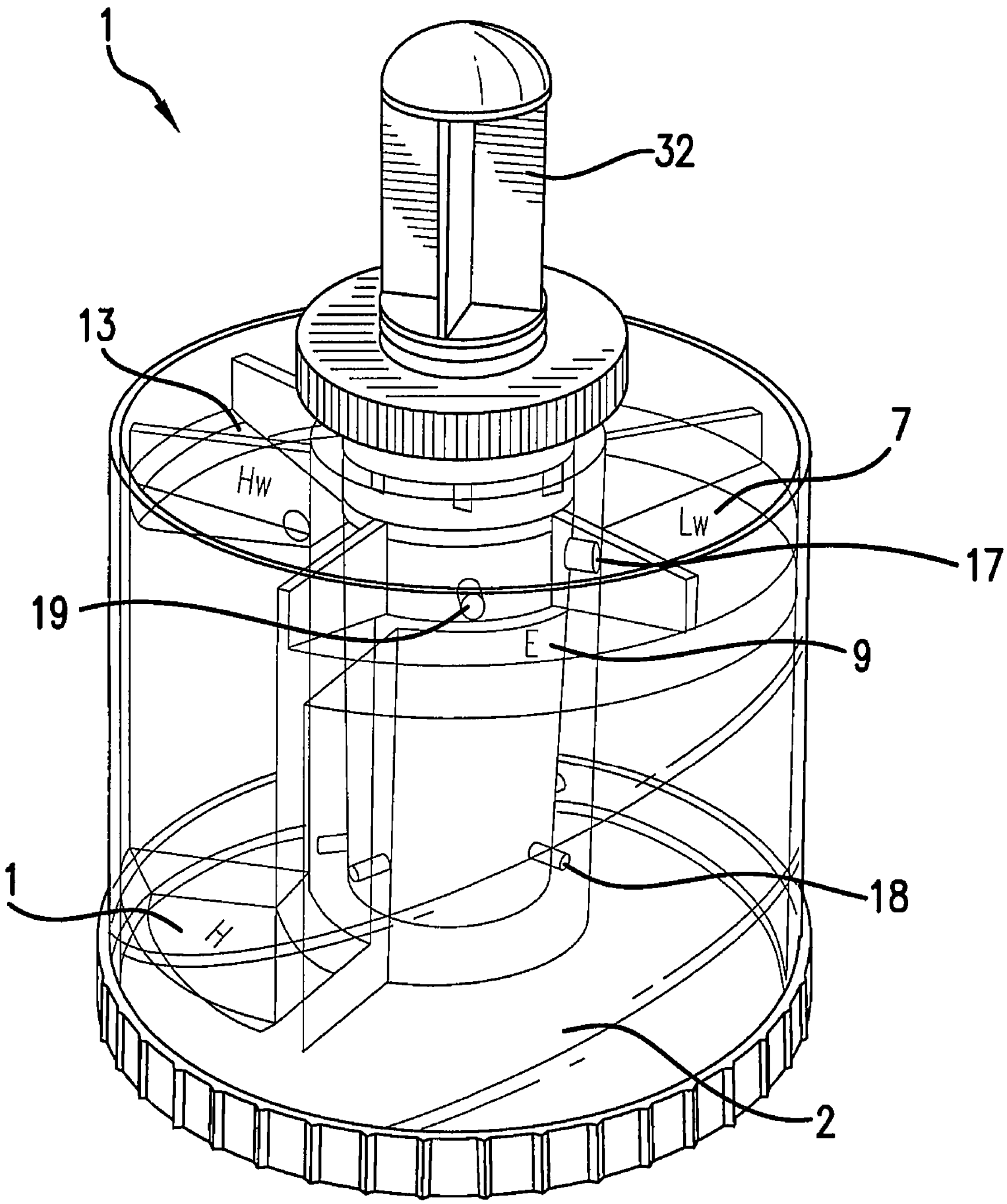
FIG. 4 is a second perspective view of the Multiplex Field Device of the present invention.
Figure 5:
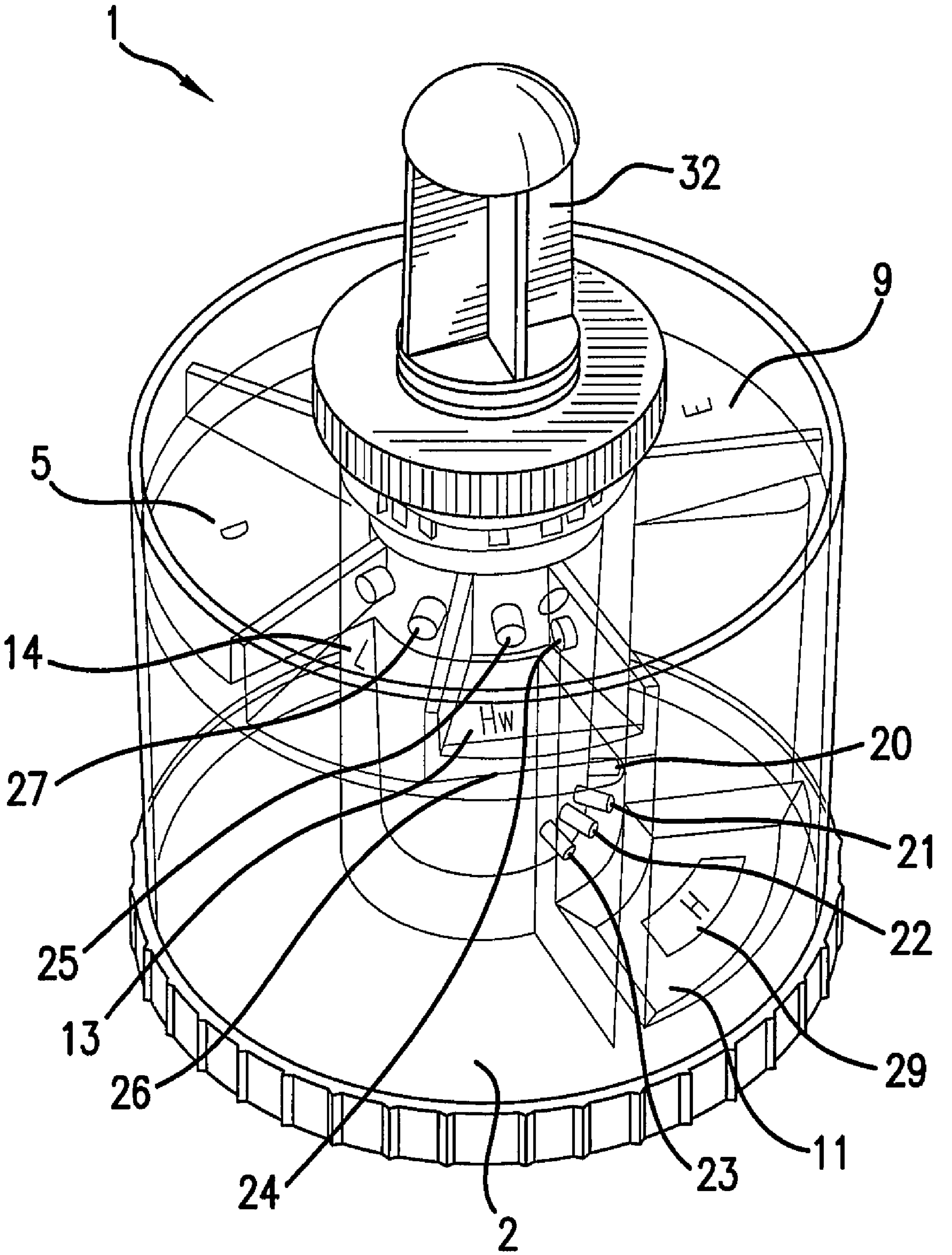
FIG. 5 is a third perspective view of the Multiplex Field Device of the present invention.

The peripheral chambers 5, 7, 9, 11, 13 and 14 and the waste chamber 2 each have at least one aperture through one of its sides, preferably the side adjacent to the central capped chamber 3. As shown in FIG. 3, aperture (D) 15 is located on a side of peripheral chamber (D) 5, waste chamber aperture (A) 16 is located on the side of wasted chamber 2, aperture (LW) 17 is located on the side of peripheral chamber (LW) 7, and waste chamber aperture (B) 18 is located on the side of waste chamber 2. Aperture 15 and aperture 17 are able to align with connecting conduit (PC) 35. Waste chamber aperture 16 and waste chamber aperture 18 are able to align with connecting conduit (WC) 37. As shown in FIG. 4, aperture (E) 19 is located on the side of peripheral chamber (E) 9 and is able to align with connecting conduit (PC) 35. As shown in FIG. 5, waste chamber aperture (C) 20 is located on the side of waste chamber 2 and aperture (Q) 21, aperture (R) 22, and aperture (S) 23 are located on a side of the hybridization chamber (H) 11. Apertures 20, 21, 22, and 23 are able to align with the connecting conduit (WC) 37 located on central capped chamber 3. As shown in FIG. 5, chamber aperture (Hw) 25 is located on a side of peripheral chamber (Hw) 13 and chamber aperture (L) 27 is located on a side of peripheral chamber (L) 14. Chamber aperture 25 and chamber aperture 27 are able to align with connecting conduit (PC) 35 by rotation of central capped chamber 3.

A first tube 24 connects peripheral chamber (H) 11 with peripheral chamber (Hw) 13. A second tube 26 connects peripheral chamber (L) 14 with peripheral chamber (H) 11.

Movement of Material

As the central capped chamber 3 is turned manually using a revolving motion, the connecting conduit (PC) 35 is able to align mutually exclusively with each of one of the following apertures: aperture 15 on a side of peripheral chamber (D) 5, aperture 17 on a side of peripheral chamber (Lw) 7, aperture 19 on a side of peripheral chamber (E) 9, aperture 25 on a side of peripheral chamber (Hw) 13, or aperture 27 on a side of peripheral chamber (L) 14. It is preferred that there is no aperture on the side of peripheral chamber (H) 11 that aligns to the connecting conduit (PC) 35. At the same time, as the central capped chamber 3 is turned or rotated, the connecting conduit (WC) 37 is able to align mutually exclusively with each one of the following apertures: waste chamber aperture 16, waste chamber aperture 18, waste chamber aperture 20, and aperture 21, aperture 22, and aperture 23 which are located in hybridization chamber 11.

Movement of Material from a Peripheral Chamber to the Waste Chamber

The interior space of each peripheral chamber (D) 5 and (Lw) 7 is able to connect to the interior space of the central capped chamber 3 when the apertures 15 and 17 are aligned with the connecting conduit (PC) 35 allowing the flow of material from one of these peripheral chambers into the interior space of the central capped chamber 3. As mentioned, connecting conduit (WC) 37 on the bottom of the central chamber 3 aligns mutually exclusively with each of the several apertures upon rotation, i.e., to either waste chamber aperture 16, waste chamber aperture 18, waste chamber aperture 20, aperture 21, aperture 22, or aperture 23. The waste chamber aperture 16, waste chamber aperture 18, and waste chamber aperture 20 are located on a side the waste chamber 2 so that material will be able to flow from the interior space of the central capped chamber 3 into waste chamber 2 if the connecting conduit (WC) 37 is aligned with one of these apertures. Apertures 21, 22, and 23 are located on a side of hybridization chamber 11 so that material is able to flow from the interior space of central capped chamber 3 into the hybridization chamber 11 when one of these apertures is aligned with connecting conduit (WC) 37. Therefore, materials are capable of being moved from the interior space of a specific peripheral chamber to the waste chamber 2 by rotating the central capped chamber 3 and aligning conduit (PC) 35 with an aperture of the specific peripheral chamber and then aligning the connecting conduit (WC) 37 with one of the apertures 16, 18, or 20 of the waste chamber 2. It is preferred that material originating from peripheral chamber (D) 5 flows through waste chamber aperture 16 and that materials originating from peripheral chamber (Lw) 7 flows through waste chamber aperture 18.

Movement of Material into Peripheral Chamber (H) 11

Materials in the interior space of peripheral chamber (E) 9 are able to flow into the interior space of the central capped chamber 3 when aperture 19 is aligned with connecting conduit (PC) 35. Materials in the interior space of the central capped chamber 3 are then able to flow through the connecting conduit (WC) 37 and into peripheral chamber (H) 11 through aperture 21 when aperture 21 is aligned with connecting conduit (WC) 37.

Material is able to move out of the interior space of peripheral chamber (Hw) 13 when the connecting conduit (PC) 35 of the central capped chamber 3 is aligned with the chamber (Hw) aperture 25. Material is able to move from peripheral chamber (Hw) 13 to peripheral chamber (H) 11 through a tube 24, preferably when there is a pressure change created by the use of moving means 32.

Material is able to move out of the interior space of peripheral chamber (L) 14 when the connecting conduit (PC) 35 of the central capped chamber 3 is aligned with aperture 27. Material is able to move from peripheral chamber (L) 14 to peripheral chamber (H) 11 through tube 26, preferably when there is a pressure change created by the use of moving means 32.

Materials in Chambers

It is preferred that peripheral chamber (D) 5 contains diluting buffer, peripheral chamber (Lw) 7 contains wash buffer, chamber (E) 9 contains eluting buffer, chamber (H) 11 contains hybridization buffer, chamber (Hw) 13 contains wash buffer, and chamber (L) 14 contains a labeling buffer. Many different variations of these buffers may be used in the present invention.

Diluting Buffers

The diluting buffer is a solution that is used to extract nucleic acids from bacteria, virus, and other organisms present in a suspect sample. The formulation of the diluting buffer includes: (a) a buffer like Tris HCl-Trizma Base (at a concentration between 10 and 200 mM), and at a pH between 7-9 (alternatively, other buffer formulations such as Na-Phosphate Buffer (10 to 100 mM) in 20% SUCROSE (pH 7.0-pH8) can be used); (b) a lytic enzyme such as lysozyme (used at a concentration between 0.1 and 5 mg/ml, most preferably at 2.5 mg/ml or "Bactozol" (or "DNAzol" which is a guanidine-detergent lysing solution from Molecular Research Center Inc.) is added; (c) a mixture of proteolytic enzymes that digest the protein wall of the target microorganisms such as Pronase and/or Proteinase K in solutions between containing between 10 and 100 mg of enzyme/ml; (d) a chelator like EDTA (at concentrations typically between 1 and 10 mM); and (e) a detergent for example from the Tween family, e.g., Tween-20, Tween-40, Tween-60, etc., or others such as NP-40, Triton-X or SDS at concentration between 5-20% w/v. Alternatively, or in addition, a surfactant such as diethylene glycol monoethyl ether (DGME), ethylene glycol monobutyl ether, and N-methyl 2-pyrrolidone at concentration between 1 and 20% w/v can facilitate sample disruption and nucleic acid extraction.

Eluting Buffers

One example of an eluting buffer used in the present invention consists of either distilled water or TE buffer (Tris-EDTA buffer: 10 mM Tris, 0.1 mM EDTA, pH 7.5). The eluting buffer releases nucleic acids from the nucleic acid-binding membrane of first solid support 31.

Hybridization Buffers

One example of a hybridization buffer used in the present invention includes: (a) SCC buffer concentrated between 0.5× and 20×(20×SCC is 175.3 g/l of NaCl, 27.6 g/l NaH2PO$_4$, and 7.4 g/l EDTA, pH 7.4); (b) 40 mM PIPES (pH 6.4); (c) a chelator such as EDTA (1 mM, pH 8.0); (d) salt, 0.4M NaCl; and (e) formamide (at concentrations between 10 and 80% v/v). An alternative hybridization buffer can consist of (a) 50 mM KCl; (b) 10 mM Tris-Cl pH 8.3; (c) 1.5 mM $MgCl_2$ (a variety of other buffers and salts can be and have been used with similar results); (d) a detergent such as SDS (0.1 to 1%), or Triton, Tweeen, or NP-40 (at concentrations between 0, 1% and 5%) can be used to facilitate wetting the hybridization membrane, accelerating the hybridization; (e) Formamide (between 20 and 80% v/v) and/or (f) other adjuvants like dextran sulfate (between 1% and 15%), Ficoll (Type 400 Pharmacia, between 0.5 and 5%), polyvylpyrrolidone (between 0.5 and 5%), protein [in the range between 0.05% and 5%, or bovine serum albumin(BSA), preferably at concentrations of 8 μg/μl, or dry milk in the range of 1% and 10%], DMSO (dimethyl sulfoxide), between 5 and 10%, glycerol (5-10%), and/or heparin (between 50 and 500 μg/ml) can be included to lower hybridization temperature, decrease background, or to speed hybridization, and; (g) non-specific nucleic acid, like salmon sperm DNA, calf thymus DNA, herring sperm DNA, calf liver DNA, or other nucleic acid is useful if placed in the hybridization mixture to reduce/block non-specific binding of target nucleic acid to the membrane. The hybridization buffer is employed after the nucleic acids have been extracted (by lyses) and purified (by binding to and elution from nucleic acid binding membranes. A range of hybridization conditions can be used depending on the stringency required with hybridization temperatures ranging from 5° C. to 70° C., preferably between 15° C. and 55° C., and more preferably between 30 and 52° C. Hybridization conditions also can be varied within two units of pH around neutral pH 7.0, preferably between pH 6.5 and 7.8, more preferable at pH 7.4.

Hybridization Wash Buffer.

One example of a hybridization wash buffer used in the present invention includes: 0.5-5% SSC v/v and 0.05-5% w/v SDS in sterile distilled water.

Labeling Buffers

Several labeling technologies can be used in chamber (L) 14 and various labeling protocols can be employed without departing from the spirit of this invention. One example of a labeling technology used in the present invention includes biotinylated probes capable of being detected with streptavidin coupled to alkaline phosphatase (AP). Streptavidin-AP conjugates capable of binding specifically and irreversibly to the biotin-labeled probes. A chromogenic substrate 0.02% BCIP (5-bromo-4-chloro-3-indolyl phosphate)/0.03% NBT (nitro blue tetrazolium) in 0.05-0.2M TBS pH 8-10, allowing the visualization of the Streptavidin AP label probes. The product of this reaction is a blue-purple precipitate that is visible by the naked eye.

Another example of labeling technology used in the present invention is Tyramide signal amplification (TSA) in combination with Molecular Probes proprietary dyes and other proprietary detection technologies. TSA is an enzyme-mediated detection method that utilizes the catalytic activity of horseradish peroxidase (HRP) to generate high-density labeling of a target nucleic acid sequence bound to a membrane. The TSA method is capable of increasing the detection sensitivity up to 100-fold, as compared with conventional avidin-biotinylated enzyme complex (ABC) that were used during first experiments.

Another example of labeling technology preferred for use in the present invention is the digoxigenin (DIG) labeling technology. A DIG label probe is first incubated in pre-hybridization buffer, consisting typically of: 3 M NaCl, 0.4 M Tris hydrochloride [pH 7.8], and 20 mM EDTA, 50×Denhardt is 1% Ficoll, 1% polyvinylpyrrolidone, and 1% bovine serum albumin in distilled water, 100 μg of denatured calf thymus DNA per ml, and 0.5% sodium dodecyl sulfate. Incubation time depends on sample volume, temperature, and presence of adjuvants (see above). By addition of formamide 50% v/v, incubation proceeds for 30 minutes under partially optimized conditions.

Various reagents can be used to develop color of DIG labeled nucleic acids for example: Anti-Dig Fab fragments, conjugated to alkaline phosphatase equilibrated in buffer and alkaline phosphatase substrate consisted of a solution A (75 mg of Nitro Blue Tetrazolium per ml of 70% dimethylformamide), a solution B (75 mg of 5-bromo-4-chloro-3-indolylphosphate, toluidine salt [Sigma], per ml of dimethylformamide), and 10 ml of equilibration buffer. Development of the dark-blue color reaction proceeds quite rapidly (generally within minutes) and color and reagents are stable under harsh conditions such as can be encountered during deployment.

Other Chromogenic Substrates (from ROCHE Diagnostics Corporation, Indianapolis, Ind.)

Can be used after Digoxeginenin labeling of the sample product and amplification of the signal with Anti-Digoxeginenin-POD (poly), Fab fragments, these other chromogenic substrates that can be used in the present invention include DAB (Diaminobenzidine (3,4,3',4'-tetraminobiphenyl)) used at 1.39 mM DAB; 0.01% H2O2 (v/v); in 50 mM Tris-HCl; pH 7.3. The reaction product is a brown, very stable water-insoluble precipitate, which is also insoluble in ethanol. In addition, BM blue POD substrate, precipitating TMB (3,3',5,5' Tetramethylbenzidine) in buffer solution, ready-to-use. The reaction product is a dark blue precipitate which is insoluble in water. All these precipitates can be seen with the naked eye, and are stable under conditions to be encountered in combat or civilian threat situations.

In addition, another example of labeling technology used in the present invention is Naphthyl red which can also be used to detect nucleic acids because the dye shows distinct chromism by hybridization with its complementary nucleic acid. Single-stranded DNA involving the Naphthyl Red moiety exhibits an orange color and has a maximal absorption at 466 nm (blue) at pH 7.0. The absorption maximum is shifted towards 545 nm (green) by the presence of its complementary DNA, and the color of the solution changes from orange to magenta accordingly. (See reference: DNA-Naphthyl Red conjugate as a visualizing probe of DNA hybridization. Asanuma H, Kashida H, Liang X, Komiyama M. Chem Commun (Camb). 2003 Jul. 7; (13):1536-1537);

Labeling Wash Buffers

Label-washing Buffers help remove unbound label from the solid support containing capture nucleic acid as used in the present invention. A preferred label wash buffer consists generally of (a) 50-100 mM Tris hydrochloride buffer (pH 7-8), (b) 150-250 mM NaCl and (c) a blocking reagent like normal sheep serum (10% w/v in phosphate-buffered saline). Another example of a label wash buffer consists of: (a) 50-70% Ethanol; (b) 20-200 mM Tris-ClH pH 7-9; (c) 5-10 M Sodium chloride or lithium chloride; and (d) a chelator such as EDTA (at a concentration between 10 and 150 mM).

Membranes (i) The First Solid Support

The first solid support or membrane 31 used in the present invention is preferably made of a material that is, or acts, as an ionic exchange, silica, or a binding agent that selectively binds nucleic acids under the proper salt or ionic conditions. The first solid support may be a nucleic acid binding membrane. Such a membrane helps purify the nucleic acids from proteins, lipids and other cellular debris. The nucleic acid binding membrane binds all the nucleic acids from any microorganism irrespective of the identity of the microbe, or its nucleic acid sequence. The forces that attach nucleic acids to this binding membrane are of physical or chemical nature (not by specific genetic complementary). The nucleic acid may be bound to the membrane surface by affinity or electro statically, for example, binding of negatively charged nucleic acid from the microbe to a positively charged surface, such as ionic exchange materials, affinity materials, silica, positively charged membranes, or positively charged columns.

(ii) The Second Solid Support

A second solid support or membrane 29, such as a hybridization membrane, is able to bind target nucleic acids by hybridization to complementary capture nucleic acids attached to the solid support. Capture nucleic acids may be attached to solid supports by several approaches. The preferred approach is by cross linking the capture nucleic acid to a solid support such as a membrane (usually by baking or UV exposure). Alternatively, capture nucleic acids may be bound to a surface by affinity. For example, binding of negatively charged capture nucleic acid to a positively charge surface, such as ionic exchange materials, affinity materials, silica, positively charged membranes, or positively charged columns. Also, capture nucleic acids may be labeled with a generic ligand to a membrane coated with the generic ligand's ligant. For example, by binding capture nucleic acids labeled with Avidin to a membrane coated with streptavidin, or vice versa.

A list of capture probes with the corresponding sequences complementary to a variety of threat biological agents has been disclosed previously. The device of the present invention was shown to work in combination with a second solid support 29 preferably in the shape of a strip or a comb filter, with the second solid support 29 having bound on its surface one or more capture nucleic acid(s). Other shapes of the second solid support 29 may be used in the present invention and be able to perform similar as described herein.

Use of Multiplex Field Device

The device of the present invention is used to facilitate the identification of a biological threat agent, in combat, or in a civilian threat situation. Rapid identification in such situations by military and/or a non-military personal is required to quickly execute the correct protective measures and clean up or decontamination procedures.

A suspect sample is identified and a soldier, or like responder, removes the moving means 32 from the multiplex field device and uncovers the central chamber 3. The multiplex field device is prepackaged with the peripheral chambers containing materials, including buffers, solutions, and other materials used in the present invention. Peripheral chamber (D) 5 contains diluting buffer, peripheral chamber (LW) 7 contains a wash buffer, peripheral chamber (E) 9 contains eluting material, peripheral chamber (H) 11 contains hybridization buffer, peripheral chamber (Hw) 13 contains a hybridization wash buffer and peripheral chamber (L) 14 contains labeling buffer. The soldier opens the cap of the central capped chamber 3 and places the suspect sample (i.e. powder, liquid, etc) into the interior space of the central capped chamber 3 and on top of the filter 30. The soldier slightly taps the device allowing fine particles (if a solid powder) to penetrate the filter and contact the first solid support 31 contained in a central chamber 3. Larger particles are retained on the filter 30. The central capped chamber 3 is position so that the connecting conduit (PC) 35 is aligned with aperture 15 in communication with peripheral chamber (D) 5. The moving means 32 is reattached and then used to create positive or negative pressure. As a result, the diluting buffer is moved from peripheral chamber (D) 5 through aperture 15 and connecting conduit (PC) 35 into the central capped chamber 3 and is incubated with the sample. The diluting material is then removed from the central capped chamber 3 through connecting conduit (WC) 37 and waste chamber aperture 16 into the waste chamber 2.

Next, central capped chamber 3 with nucleic acid bound to the binding membrane, or first solid support 31, is then rotated to communicate with a peripheral chamber (LW) 7 containing washing buffer. Communication occurs when the connecting conduit (PC) 35 aligns with an aperture 17 in the side of peripheral chamber (LW) 7. The wash buffer contained in peripheral chamber (LW) 7 is moved into the central capped chamber 3 through the aperture 17 and connecting conduit 35, washing the nucleic acids bound on the binding membrane 31. Moving means 32 is preferably used to move the washing buffer through the membrane 31 and collected in the waste chamber 2. Next, the central capped chamber 3 is rotated in such a way as to enable the alignment of connecting conduit (PC) 35 with aperture 19 located on the side of peripheral chamber (E) 9. Peripheral chamber (E) 9 contains eluting buffer. The eluting buffer passes through aperture 19 and the connecting conduit (PC) 35 into the interior of the central capped chamber 3. The eluting buffer contacts the solid support or membrane 31 and releases the bound nucleic acid(s). The released nucleic acids and eluting buffer are then moved into hybridization chamber (H) 11 when the connecting conduit (WC) 37 is aligned with aperture 20. The eluting buffer containing the target nucleic acid present mixes with the hybridization buffer present in peripheral chamber (H) 11 and allowed to incubate for 30 minutes. This incubation period allows the target nucleic acid(s) to hybridize with capture nucleic acid(s) present on the second solid support or membrane 29 present in the peripheral chamber (H) 11. The second solid support 29 contains an array of capture nucleic acid sequences complementary to the nucleic acid sequences of a series of threat biological agents, i.e., target nucleic acid sequences. Only specific target nucleic acid sequences with complementary sequences to the capture nucleic acid sequences will bind to the second solid support 29.

After the incubation is completed, the material and all the nucleic acid sequences that do not correspond to the capture nucleic acid sequences are removed from peripheral chamber (H) 11 by use of the moving means 32. The central capped chamber 3 is rotated in a clockwise direction aligning connecting conduit (WC) 37 and aperture 22, which leads directly to the waste chamber 2 where the mixture is sent by use of the moving means 32 which may comprise a pump.

The second solid support 29 with specific nucleic acids attached is washed with hybridization wash buffer. The central capped chamber 3 is rotated in clockwise direction to enable alignment of connecting conduit (PC) 35 with aperture 25 of peripheral chamber (Hw) 13. This enables the hybridization wash buffer to move from peripheral chamber (Hw) 13 to peripheral chamber (H) 11 through tube 24 by way of pressure change. The hybridization wash buffer is then removed after covering the hybridization membrane by reversing the moving means 32.

Immediately thereafter, the operator rotates the central capped chamber 3 clockwise to align the connecting conduit (PC) 35 with peripheral chamber (L) 14 through aperture 27. This enables the labeling solution to move from peripheral chamber (L) 14 to peripheral chamber (H) 11 through tube 26 by way of a pressure change through the use of the moving means 32. The labeling solution is preferably a solution of secondary specific probes (preferably labeled with digoxigenin). Other conventional labeling solutions and probes may be used. Thus, the labeling solution is brought from chamber (L) 14 onto the hybridization membrane 29 in chamber (H) 11 and nucleic acids specifically hybridized to the membrane 29 are labeled by incubating for a time of approximately 15 minutes or until nucleic acids in membrane 29 can be visualized as dots by the naked eye. The identity of biological threat agents will be identified by the array of color produced on the solid support or membrane 29. A key on the back of the device (or on another convenient location) based on an array of colors produced identifies a specific biological threat agent. A soldier or other user simply compares the array of color seen on the solid support 29 to the key and the key tells the user if there is one or more biological threat agents in the sample.

The processing of the sample is attained by simply lifting and lowering a piston or pistons (syringe type of moving means 32) comprising integral parts of the device and rotating the central chamber 3 relative to the surrounding chambers with reagents appropriate for each analytical step. Rotation is made by the operator manually without additional sources of energy, but electrical or electronic operation can be envisioned without departing from the spirit of the present invention. A series of conduits and ports allow fluid transfer between aligning chambers. After processing the sample, a signal corresponding to a biological threat agent can be observed by visual inspection by the naked eye, i.e., of stains or colors in membrane 29 within the device. The use of nucleic acid sensors able to discriminate the presence of target nucleic acids hybridized to a membrane from background signals in the absence of target can be eventually used without departing from the spirit of the present invention. Once used, the device is disposable. Infectious organisms, once inside the device, are degraded to their nucleic acid constituents rendering any organism non-infectious and the operation of the device safe. Since the device is self contained (contains all needed reagents) and operator powered, the device does not need any substantial logistic support.

Additional chambers may be added to the present invention. For example, such chambers that could hold additional solutions such as wash buffer, label solutions, etc.

Although the present invention has been described in detail with reference to examples above, it is understood that various modifications can be made without departing from the spirit of the invention. Accordingly, the invention is limited only by the following claims. All cited patents, patent applications and publications referred to in this application are herein expressly incorporated by reference in their entirety.

What is claimed is:

1. A multiplex field device for detecting biological threat agents, comprising:

(a) a central capped chamber having a top, a bottom, a connecting conduit (PC), and a connecting conduit (WC), wherein the connecting conduit (PC) and the connecting conduit (WC) are located between the top and the bottom;

(b) a plurality of peripheral chambers surrounding said central capped chamber, each of said plurality of peripheral chambers having at least one aperture; and (c) a waste chamber surrounding said central capped chamber, said waste chamber including a plurality of apertures:

(d) wherein said connecting conduit (PC) is able to align with the apertures of the peripheral chambers and said connecting conduit (WC) is able to align with the apertures of the waste chamber and a peripheral chamber.

2. The multiplex field device of claim 1, wherein said plurality of peripheral chambers comprises: a first peripheral chamber including a first aperture; second peripheral chamber including a second aperture; a third peripheral chamber including a third aperture; a fourth peripheral chamber including three apertures comprising aperture (Q), aperture (R), and aperture (S); a fifth peripheral chamber including a fifth aperture; and a sixth peripheral chamber including a sixth aperture; a first tube or conduit connecting the fourth peripheral chamber to the fifth peripheral chamber, and a second tube or conduit connecting the fourth peripheral chamber to the sixth peripheral chamber; and wherein said waste chamber plurality of apertures comprises three apertures comprising aperture (A), aperture (B) and aperture (C).

3. The multiplex field device of claim 1, further comprising a means for moving material through said device selected from the group consisting of a syringe, an embolus, or any means for creating a pressure change through said device.

4. The multiplex field device of claim 1, wherein the central capped chamber further comprises a filter and a first solid support, said filter and support contained within the central capped chamber and wherein said filter is positioned above said fast solid support.

5. The multiplex field device of claim 4, wherein said first solid support comprises a nucleic acid binding membrane.

6. The multiplex field device of claim 2, wherein the central capped chamber is able to rotate on an axis.

7. The multiplex field device of claim 6, wherein the connecting conduit PGjEca is able to align with the first aperture, the second aperture, the third aperture, the fifth aperture, or the sixth aperture one at a time as the central chamber is rotated around the axis.

8. The multiplex field device of claim 6, wherein the connecting conduit (WC) is able to align with aperture (Q), aperture (R), aperture (S), aperture (A), aperture (B) or aperture (C) one at a time as the central chamber is rotated around the axis.

9. The multiplex field device of claim 2, wherein a second solid support is located in the fourth peripheral chamber.

10. The multiplex field device of claim 9, wherein said second solid support comprises a hybridization membrane having one or more capture nucleic acid sequences attached thereto.

11. A multiplex field device for detecting biological threat agents, comprising:

(a) a central capped chamber comprising a top, a bottom, a connecting conduit (PC), a connecting conduit (WC), a first solid support, and a filter;

(b) a plurality of peripheral chambers surrounding said central capped chamber comprising a first peripheral chamber including a first aperture; a second peripheral chamber including a second aperture; a third peripheral chamber including a third aperture; a fourth peripheral chamber including three apertures comprising aperture (Q), aperture (R), and aperture (S); at a fifth peripheral chamber including a fifth aperture; and a sixth peripheral chamber including a sixth aperture;

(c) a first tube or conduit connecting the fourth peripheral chamber to the fifth peripheral chamber;

(d) a second tube or conduit connecting the fourth peripheral chamber to the sixth peripheral chamber;

(e) a second solid support disposed within said fourth peripheral chamber, and (f) a waste chamber surrounding said central capped chamber, said waste chamber including three apertures comprising aperture (A), aperture (B), aperture (C), and wherein the central chamber is able to rotate on its axis;

(g) wherein the connecting conduit (PC) is able to align with the first aperture, the second aperture, the third aperture, the fifth aperture, or the sixth aperture one at a time as the central chamber is rotated around the axis; and (h) wherein the connecting conduit (WC) is able to align with aperture (Q), aperture (R), aperture (S), aperture (A), aperture (B), or aperture (c) one at a time as the central chamber is rotated around the axis.

12. The multiplex field device of claim 11, further comprising means for moving material through said device selected from the group consisting of a syringe, an embolus, or any means for creating a pressure change through the device.

13. The multiplex field device of claim 11, wherein the second solid support comprises a nucleic acid hybridization membrane having one or more capture nucleic acid sequences attached thereto.

14. The multiplex field device of claim 11, wherein said first solid support comprises a nucleic acid binding membrane.

15. A kit comprising:

(a) multiplex field device of claim 11; and (b) materials comprising a diluting buffer present in the first peripheral chamber, a wash buffer present in the second peripheral chamber, an eluting buffer present in the third peripheral chamber; a hybridization buffer present in the fourth peripheral chamber, a hybridization wash buffer present in the fifth peripheral chamber, and a labeling buffer present in the sixth peripheral chamber.

16. The kit of claim 15, further comprising a means for moving material through said device selected from the group consisting of a syringe, an embolus, or any device for creating a pressure change through the chambers.

17. The kit of claim 15, wherein the labeling buffer comprises digoxenin.

18. A method of detecting a biological threat agent, comprising:

(a) obtaining a suspect sample;

(b) placing the suspect sample into the central chamber of the kit of claim 15;

(c) rotating the central capped chamber so that diluting buffer is moved into the interior of the central capped chambered and then moved into the waste chamber;

(d) rotating the central capped chamber so that wash buffer is moved into the interior of the central capped chambered and then moved out into the waste chamber, (e) rotating the central capped chamber so that eluting buffer is moved into the interior space of the central capped chamber and then is moved out so as to come in contact with the second solid support in the fourth peripheral chamber;

(f) rotating the central capped chamber so that the hybridization wash is moved and contacts the second solid support and then is moved into the waste chamber;

(g) rotating the central capped chamber so that the labeling buffer is moved and contacts the second solid support;

(h) visually inspecting the second solid support; and (i) identifying the biological threat agent.

19. The method of claim 18, wherein the suspect sample was obtained from a combat or terrorist threat situation.

* * * * *